(12) United States Patent
Perouse

(10) Patent No.: US 6,387,133 B1
(45) Date of Patent: May 14, 2002

(54) RECONSTRUCTION IMPLANT

(75) Inventor: Eric Perouse, L'Isle Adam (FR)

(73) Assignee: Laboratoire Perouse Implant, Bornel (FR)

(*) Notice: Subject to any disclaimer, the term of this patent is extended or adjusted under 35 U.S.C. 154(b) by 0 days.

(21) Appl. No.: 09/353,789

(22) Filed: Jul. 15, 1999

(30) Foreign Application Priority Data

Jul. 16, 1998 (FR) .............................. 98 09112

(51) Int. Cl.⁷ .................................................. A61F 2/04
(52) U.S. Cl. ............................... 623/23.64; 623/23.67; 623/8
(58) Field of Search .................... 623/23.64, 23.67, 623/8, 23.65, 23.68

(56) References Cited

U.S. PATENT DOCUMENTS

| | | | |
|---|---|---|---|
| 4,902,294 A | * 2/1990 | Gosserez | 623/8 |
| 5,141,581 A | * 8/1992 | Markham | 623/7 |
| 5,282,857 A | * 2/1994 | Perry et al. | 623/8 |
| 5,496,370 A | * 3/1996 | Hamas | 623/23.67 |
| 5,843,189 A | * 12/1998 | Perouse | 623/8 |

FOREIGN PATENT DOCUMENTS

WO 95/23565 9/1995

* cited by examiner

*Primary Examiner*—Corrine McDermott
*Assistant Examiner*—Brian E Pellegrino
(74) *Attorney, Agent, or Firm*—Wenderoth, Lind & Ponack, L.L.P.

(57) ABSTRACT

A reconstruction implant (10) of predetermined shape has a deformable outer envelope (12) containing a filler liquid (15) whose viscosity is substantially equal to that of water. The thickness of the envelope (12) is sufficient to confer on the envelope a shape substantially identical to the predetermined shape in the absence of the filler liquid. The pressure of the filler liquid contained in the envelope (12) is substantially equal to the pressure outside the envelope. The implant can be used as a testicle prosthesis.

20 Claims, 1 Drawing Sheet ns a reconstruction implant
RECONSTRUCTION IMPLANT

BACKGROUND OF THE INVENTION

The present invention concerns a reconstruction implant of predetermined shape, of the type having a deformable external envelope containing a filler liquid whose viscosity is substantially equal to that of water.

Such implants are used in humans to replace a gland whose ablation has been rendered necessary by disease or accident, for example. Such implants are intended in particular to replace a testicle or a mammary gland.

Other reconstruction implants of the aforementioned type are used to replace a damaged muscle or for artificial augmentation of the apparent volume of a muscle.

Prior art testicular implants generally have a deformable outer envelope of cross-linked silicone. This envelope defines a closed housing in which a silicone gel is confined.

In prior art implants the thickness of the envelope is in the range from 0.4 mm to 0.7 mm. In practice the envelope is as thin as possible, the consistency of the testicle being obtained by the viscosity of the gel contained in the envelope. The viscosity of a gel of this kind is in the order of a few Pascal.seconds.

Because of the poor public image of silicone gel, implants, and artificial testicles in particular, have been filled with physiological serum instead of silicone gel.

The viscosity of the physiological serum is close to that of water. Accordingly, to assure a satisfactory consistency of the implant on palpation, the pressure of the physiological serum in the envelope has been increased.

The thin envelope, whose thickness is in the range 0.4 mm to 0.7 mm, is then tensioned by the increased pressure of the physiological serum. The resulting turgidity of the implant obtained in this way reproduces the shape and consistency of the organ it replaces fairly faithfully.

The existence of an increased pressure inside the envelope causes premature aging of the implant. The pressure is seen to reduce progressively due to the effect of migration of the physiological serum through the envelope. The consistency and the shape of the implant therefore deteriorate with time.

SUMMARY OF THE INVENTION

The aim of thee invention is to provide a reconstruction implant using a filler liquid whose viscosity is substantially equal to that of water and whose consistency remains close to that of the organ to be replaced.

To this end, the invention consists in a reconstruction implant of predetermined shape, of the aforementioned type, characterized in that the thickness of said envelope is sufficient to confer on said open envelope a shape substantially identical to said predetermined shape in the absence of the filler liquid and in that the pressure of the filler liquid contained in said closed envelope is substantially equal to the pressure outside the envelope.

The particular embodiment of the reconstruction implant has one or more of the following features:

the thickness of the envelope is made such that the ratio of the greatest dimension of the implant to the thickness of the envelope is in the range from 2.3 to 20;

the thickness of the envelope is made such that the ratio of the greatest dimension of the implant to the thickness of the envelope is in the range from 5 to 18;

the envelope includes a silicone membrane whose thickness is greater than 2.5 mm;

the thickness of the envelope is in the range from 2.5 mm to 7.5 mm;

the greatest dimension of the implant is in the range from 2 cm to 5 cm;

the filler liquid is physiological serum;

said predetermined shape is an oval shape and corresponds to the shape, of a testicle.

BRIEF DESCRIPTION OF THE DRAWINGS

The invention better understood on reading the following description which is given by way of example only and with reference to the drawings, in which.

DETAILED DESCRIPTION OF THE INVENTION

Figure 1:
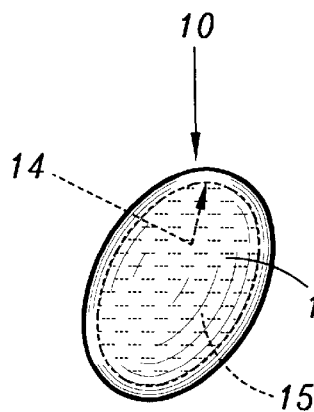
FIG. 1 is a perspective view of a testicle in accordance with the invention.

The testicle 10 shown in FIG. 1 is of oval shape. It has a thick envelope 12 delimiting a closed housing 14 filled with a filler liquid 15. The filler liquid 15 is advantageously physiological serum. The viscosity of the liquid 15 is substantially equal to that of water, i.e. approximately $10^{-3}$ Pa.s. It is confined in the housing 14 without air and at a pressure substantially equal to atmospheric pressure.

Figure 2:
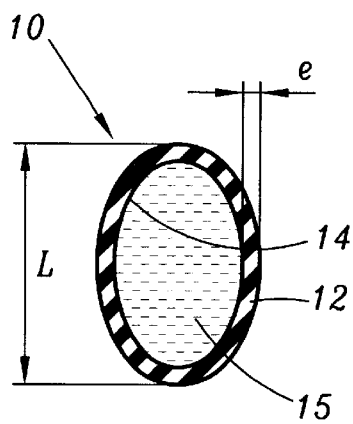
FIG. 2 is a view of the testicle from FIG. 1 in longitudinal section.

FIG. 2 shows the testicle 10 in cross section. The testicle 10 has a length L equal to 3.5 cm in the direction of its largest dimension. The membrane forming the envelope 12 has a constant thickness e equal to 2.5 mm. The envelope is made from a polymer material, in particular cross-linked silicone.

The thickness of the membrane forming the envelope 12 is sufficient to confer on the open envelope in the absence of the filler liquid a shape substantially identical to the final shape of the testicle.

Accordingly, for an open envelope, i.e. an envelope filled with air and having at least one hole in it through which the air can flow, the envelope 12 defines a self-supporting shell reproducing the shape of the implant when no external load other than atmospheric pressure is applied.

To this end, the envelope comprises a silicone membrane whose thickness e is greater than 2.5 mm. The thickness of the envelope is advantageously in the range from 2.5 mm to 7.5 mm.

To make the envelope strong enough, its thickness is chosen so that the ratio of the greatest dimension L of the implant to the thickness e of the envelope is in the range from 2.3 to 20 and advantageously in the range from 5 to 18.

FIGS. 3 to 6 show various testicles with varying dimensions and envelope thicknesses.

The greatest dimension of human testicles is in the range from 2 cm to 5 cm.

Figure 3:
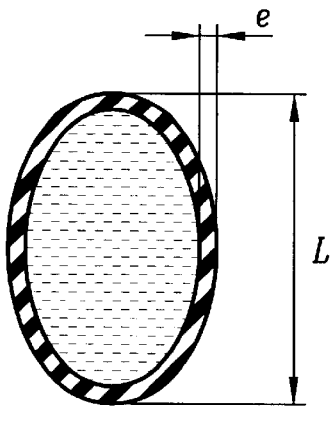
FIGS. 3 to 6 are views in longitudinal section of variants of a testicle in accordance with the invention.

FIG. 3 shows a testicle with a greatest dimension L equal to 4.5 cm. The thickness e of the envelope is 2.5 mm. For a testicle of this kind, the ratio of the greatest dimension L to the thickness e is equal to 18. Despite this high ratio, the open envelope without the filler liquid is sufficiently rigid to impose the shape of the testicle.

The shape of the envelope is maintained for ratios of the greatest dimension of the implant to the thickness e of the envelope less than 20.

Figure 4:
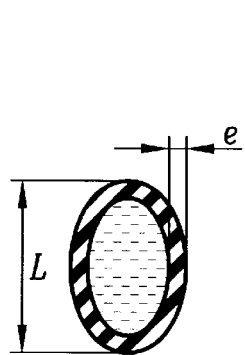

FIG. 4 shows a small testicle whose greatest dimension L is equal to 2.5 cm. The wall thickness e is 2.5 mm.

A testicle of this kind, filled with physiological serum at atmospheric pressure feels harder than the testicle from FIG. 3. This is because the ratio of the maximum dimension L to the thickness e is greater.

Figure 5:
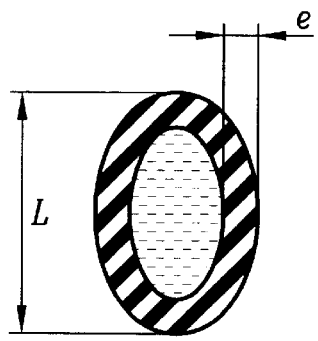
Figure 6:
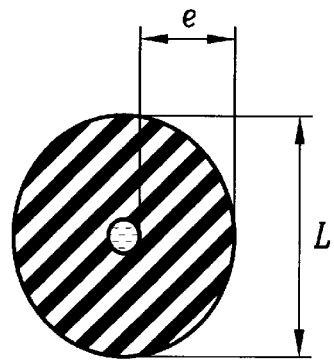

FIGS. 5 and 6 show two other examples of testicles in which the greatest dimension L is equal to 3.5 cm. Their thickness e is respectively 5 mm and substantially 15 mm. They are both filled with physiological serum at atmospheric pressure.

The testicle from FIG. 6 feels harder than that from FIG. 5 because of the greater thickness e of the envelope, although both testicles have the same maximum dimension.

Clearly the hardness of the testicle can be increased by increasing the thickness e of the envelope without it being necessary to modify the pressure of the filler liquid, which is always equal to atmospheric pressure.

The absence of suspension in the housing 14 is made possible by the stiffness imparted by the thick envelope 12 which forms a shell. Accordingly, the shape and hardness of an implant in accordance with the invention are provided essentially by the envelope 12 and not by the filler liquid. This is why the thickness of the membrane forming the envelope must be sufficient to guarantee the stability of the profile of the implant when the housing 14 is open without the filler liquid.

With such implants, the filler liquid being at atmospheric pressure, no migration through the envelope occurs. Accordingly, the hardness of the implant when palpated remains constant with time.

Figure 7:
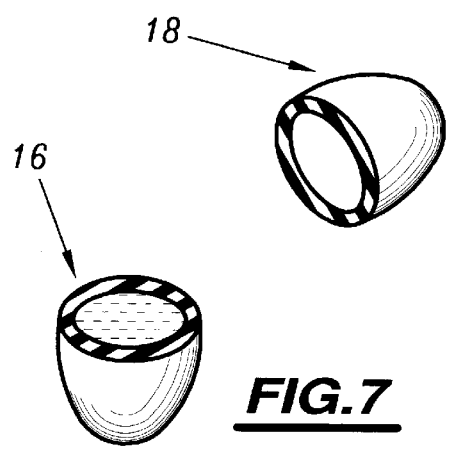
FIG. 7 is a perspective view of two half-shells adapted to be assembled together to form a testicle in accordance with the invention.

To manufacture a testicle in accordance with the invention two identical half-shells 16, 18 are initially made (see FIG. 7). These half-shells are molded. Each is substantially hemispherical.

Figure 8:
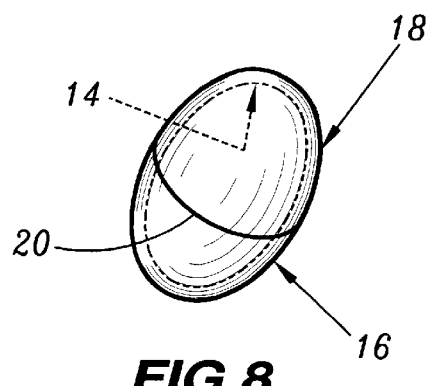
FIG. 8 is a perspective view of the assembled testicle.

As shown in FIG. 8, the half-shells 16, 18 are joined together to form the envelope 12. They are joined together by gluing them together at an equatorial joint plane 20, for example.

The closed housing 14 defined between the two half-shells 16, 18 is then totally filled with physiological serum using a syringe. The filling is carried out from the bottom of the testicle and a vent is formed at the top of the testicle to evacuate the air contained in the housing.

The hole made by the needle of the injection syringe and the vent are closed when the testicle has been filled completely by drops of elastomer that can be cross-linked when cold.

In another embodiment of the invention the envelope of the testicle is made in one piece by successively dipping a fusible core into a bath of silicone that can be cross-linked cold. After the fusible core has been extracted, the testicle is filled with physiological serum in a similar manner to that previously described.

In a further variant of the invention, the envelope 12 can be formed by rotational molding from an elastomer which can be cross-linked hot or cold.

The implant in accordance with the invention is illustrated here by an artificial testicle. Reconstruction implants in the shape of the calf muscle or any other muscle can be made with a structure in accordance with the invention.

What is claimed is:

1. A reconstruction implant of predetermined shape, comprising:
    a deformable outer envelope including a silicone membrane whose thickness (e) is greater than 2.5 mm; and
    a filler liquid contained in said outer envelope and having a viscosity substantially equal to that of water;
    wherein said filler liquid is contained in said outer envelope so as to have a pressure substantially equal to a pressure outside of said outer envelope; and
    wherein said outer envelope has a thickness sufficient that, even without said filler liquid contained in said outer envelope, said outer envelope would maintain a shape substantially identical to said predetermined shape.

2. A reconstruction implant according to claim 1, wherein the thickness (e) of the envelope is such that the ratio of the greatest dimension (L) of the implant to the thickness (e) of the envelope is in the range from 2.3 to 20.

3. A reconstruction implant according to claim 2, wherein the filler liquid is physiological serum.

4. A reconstruction implant according to claim 2, wherein said predetermined shape is an oval shape and corresponds to the shape of a testicle.

5. A reconstruction implant according to claim 2, wherein the thickness (e) of said envelope is substantially uniform throughout.

6. A reconstruction implant according to claim 1, wherein the thickness (e) of the envelope is such that the ratio of the greatest dimension (L) of the implant to the thickness (e) of the envelope is in the range from 5 to 18.

7. A reconstruction implant according to claim 6, wherein the filler liquid is physiological serum.

8. A reconstruction implant according to claim 6, wherein said predetermined shape is an oval shape and corresponds to the shape of a testicle.

9. A reconstruction implant according to claim 6, wherein the thickness (e) of said envelope is substantially uniform throughout.

10. A reconstruction implant according to claim 1, wherein the thickness (e) of the envelope is in the range from 2.5 mm to 7.5 mm.

11. A reconstruction implant according to claim 10, wherein the greatest dimension (L) of the implant is in the range from 2 cm to 5 cm.

12. A reconstruction implant according to claim 10, wherein the filler liquid is physiological serum.

13. A reconstruction implant according to claim 10, wherein said predetermined shape is an oval shape and corresponds to the shape of a testicle.

14. A reconstruction implant according to claim 1, wherein a greatest dimension (L) of the implant is in the range from 2 cm to 5 cm.

15. A reconstruction implant according to claim 14, wherein the filler liquid is physiological serum.

16. A reconstruction implant according to claim 14, wherein said predetermined shape is an oval shape and corresponds to the shape of a testicle.

17. A reconstruction implant according to claim 1, wherein the filler liquid is physiological serum.

18. A reconstruction implant according to claim 17, wherein said predetermined shape is an oval shape and corresponds to the shape of a testicle.

19. A reconstruction implant according to claim 1, wherein said predetermined shape is an oval shape and corresponds to the shape of a testicle.

20. A reconstruction implant according to claim 1, wherein the thickness (e) of said envelope is substantially uniform throughout.

* * * * *